United States Patent [19]

Oppenheimer et al.

[11] Patent Number: 5,399,500
[45] Date of Patent: Mar. 21, 1995

[54] TWO STEP PROCESS FOR COATING OF ANTIBODIES TO A SOLID PHASE

[75] Inventors: Leslie Oppenheimer, Kinnelon, N.J.; Lewis R. Pollack, Riverdale, N.Y.

[73] Assignee: Becton Dickinson and Company, Franklin Lakes, N.J.

[21] Appl. No.: 906,213

[22] Filed: Jun. 26, 1992

[51] Int. Cl.$^6$ ............... G01N 33/543; G01N 33/545
[52] U.S. Cl. ................... 436/500; 435/7.92; 436/518; 436/531
[58] Field of Search ............ 436/500, 518, 531, 500; 435/7.92

[56] References Cited

U.S. PATENT DOCUMENTS

| | | | |
|---|---|---|---|
| 4,092,408 | 5/1978 | Litt | 436/531 |
| 4,166,844 | 9/1979 | Tu . | |
| 4,256,724 | 3/1981 | Rutner et al. . | |
| 4,360,358 | 11/1982 | Sharma . | |
| 4,481,298 | 11/1984 | Cone, Jr. et al. | 435/7.93 |
| 4,829,009 | 5/1989 | Graves | 436/518 |

OTHER PUBLICATIONS

Kapyaho, P. et al., Scand. J. Clin. Lab. Lab. Invest. 49; Effect of complement binding on a solid-phase immunometric TSH assay (1989), pp. 211–216.

Sarma, J. et al., Life Sciences, vol. 38, Enzyme Linked Immuno sorbent Assay (ELISA) for B–Endorphin and Its Antibodies, pp. 1723–1732.

Oshima, M. et al., Immunological Investigatons, 18(7), Comparison of Peptide-Coating Conditions in Solid Phase Plate Assays for Detection of Anti-Peptide Antibodies, (1989) 841–851.

Sankolli, G. M. et al., Journal of Immunological Methos, 104, Improvement in the antibody binding characteristics of microtitre wells by pretreatment with anti--IgG Fc immunoglobulin, (1987) pp. 191–194.

Lovborg, U., Guide to Solid Phase Immunoassays.

*Primary Examiner*—David Saunders
*Attorney, Agent, or Firm*—Susan A. Capello; Royal N. Ronning, Jr.

[57] ABSTRACT

A process for coating an antibody on a substrate includes two steps. A secondary antibody to a primary antibody is coated on the substrate followed by a coating with primary antibody in the presence of blocking and stabilizer agents.

15 Claims, No Drawings

TWO STEP PROCESS FOR COATING OF ANTIBODIES TO A SOLID PHASE

BACKGROUND OF THE INVENTION

The invention relates to a method for coating antibodies on a substrate for the assay of antigens.

Immunoassays are used to quantify antigens or antibodies by immunochemical means. Generally, a varying quantity of either antigen or antibody is added to a constant amount of the other with the formation of an antigen-antibody complex measured as a function of the varied reactant represented by a standard curve for the varied reactant. The reaction of an unknown amount of the varied reactant can then be referred to the standard curve to obtain the amount of varied reactant which produces a comparable change.

The antibody-antigen complex may form in solution (homogeneous assay) or one of the reactants can be attached to a solid support (heterogeneous assay). The heterogeneous assay generally utilizes a wash step in which uncomplexed material is removed. The present invention pertains only to heterogeneous assays.

In immunoassays, either the antibody or the antigen may be initially affixed to a solid support, such as a plastic surface or beads, to facilitate separation of the antigen-antibody reaction product from unreacted material in immunosorbent assays called solid phase immunoassays. The present invention is concerned with the affixation of antibodies to a solid support.

In solid phase immunoassays, various substances such as fluorochomes, isotopes or enzymes have been used to label antigens or antibodies as a means to detect the antibody-antigen association, for example, fluorescence immunoassay (FIA), radioimmuno-assay (RIA), immunoradiometric assay (IRMA), enzyme immunoassay (EIA), enzyme-linked immunoassay (ELISA), and the biotin-avidin system. Liposomes have also been used as inert reagents to facilitate detection of reaction by incorporating the antigen or antibody into the surface of artificial membranes.

Several methods have been devised for coating a solid phase with an antibody in preparation for solid phase immunoassay. The simplest method is a one step procedure in which a primary antibody is coated in a nonspecific, non-oriented fashion directly onto the surface of a solid phase. This one-step, antibody coated surface is then used to assay for an antigen. (See, e.g., K. J. Catt et al., Nature, 213, 825 ( 1967).

A refinement in the above-described preparation for immunoassays is proper orientation of the primary (capture) antibody for optimal assay sensitivity when the antibody is contacted with antigen. This has been accomplished by use of a secondary antibody which is capable of binding the primary antibody distal to the antigen binding site.

Secondary antibodies may be affinity purified and Fc-specific to a primary antibody. The Fc portion of an immunoglobin (Ig) monomer corresponds to the stem of the Y-shaped Ig molecule and consists of the C-terminal sections of the two heavy chains linked by one or more disulfide bonds. It is the site of complement fixation in complement-fixing antibodies. Fc-specificity enables the primary antibody to bind to the secondary antibody in optimal Fab orientation for immunoassay of the antigen. The Fab portion of an Ig consists of a light chain linked via disulfide bond to the N-terminal part of the heavy chain, i.e. it is one of the two limbs of the Y-shaped Ig molecule. Each Fab portion of an antibody contains a single combining site.

In a multiple coating process, a surface may be first precoated with a secondary antibody which is an anti-antibody to a primary antibody. The pre-coated surface is then coated with the primary antibody to an antigen and the two-coated surface used to assay for the antigen. A method of this type is described, for example, in U.S. Pat. Nos. 4,092,408, and 4,166,844 and by G. M. Sankolli, et al., "Improvement in the Antibody Binding Characteristics of Microtitre Wells by Pretreatment With Anti-IgG Fc Immunoglobin" J. Imm. Meth , 104,191–194 (1987). The coating with secondary and primary antibody may also be simplified by combining the two antibodies into a single-step cocoating process.

When a coating on a solid phase is used in immunoassays, nonspecific binding to unoccupied spaces on the solid surface may interfere with the accuracy, precision or sensitivity of the assay and result in high backgrounds and false read-outs. Blocking agents have been used in a separate coating step to block nonspecific binding sites. Bovine serum, albumin, gelatin, casein, and other substances have been used as blocking agents. This blocking step may be called a postcoat. The postcoating step has traditionally been undertaken after the primary antibody has been applied to the solid surface. In this instance, it can be a 2 step process involving a simple primary antibody coat and a blocking agent-post coat; or a three step process consisting of a secondary antibody precoat, a primary antibody coat, and a blocking agent post coat. If the precoat and coat steps are combined (cocoat), a two step process results with a secondary and primary antibody cocoat in the first step and a blocking agent postcoat in the second step.

A superior coating process using a different sequence of steps has now been discovered.

It is an object of the invention to provide an efficient coating process with a minimum of procedural steps and optimally oriented capture antibody.

It is another object to provide an immunoassay with an increased dynamic range.

An additional object of this invention is to minimize the extent of purification of the primary antibody. Since it is bound directly to the secondary antibody already on the substrate, the primary antibody does not have to compete for binding sites with contaminating proteins.

Another object of this invention is to improve assay response over "traditional" coating methods. The dynamic range is improved over the conventional cocoat-postcoat or precoat-coat-postcoat processes.

Minimized use of primary antibody is yet another object of this invention.

SUMMARY OF THE INVENTION

Accordingly, there is provided a process for coating a primary antibody on a substrate by first contacting a secondary antibody with a substrate surface which is capable of binding the secondary antibody to form a secondary antibody-coated substrate. The secondary antibody-coated substrate is then contacted with a primary antibody to which the secondary antibody is specific, blocking agent, and optionally, a stabilizing agent, thereby providing a stable substrate surface coated with secondary antibody bound to primary antibody, with non-specific binding sites blocked.

Advantageously and unexpectedly, the new coating method has improved sensitivity while utilizing a minimum of steps and requiring a minimum amount of primary antibody. It is thereby particularly useful in industrial applications.

For a better understanding of the present invention, together with other and further objects, reference is made to the following description, and its scope will be pointed out in the appended claims.

DETAILED DESCRIPTION OF THE INVENTION

The present invention provides a method for preparing antibody coated substrates for use in solid phase immunoassays.

For this specification, the following will be understood: Coating is the direct application of a primary antibody to a surface. Precoating is the application of a coat of secondary antibody to a support. Cocoating is the concurrent application of more than one antibody at the same time. Postcoating has traditionally been a separate step and is the application of a blocking agent to an antibody-coated surface.

Examples of primary antibodies which are coated on the support may be polyclonal or monoclonal antibodies to any antigen of interest. Steroids such as testosterone, androsterone, progesterone, estrone, estradiol, estriol, deoxycorticosterone, cortisol, cortisone, aldosterone, etc.; cardiotonic glycosides such as digoxin, digitoxin, ouabain, deslanoside and their aglycones; hormones such as thyroid-stimulating hormone (TSH), $T_4$ and $T_3$; vitamins such as B, C, E, K and folic acid, etc.; biologically active molecules, drugs and their metabolites; pathogens; and toxins or other antigens are of interest. It is also an advantage of the invention that the method is applicable to both small molecules (e.g. $T_4$, $T_3$ uptake, digoxin, theophylline) which are usually assayed in a competitive format, and larger molecules such as thyroid stimulating hormone (TSH), which are usually assayed in a "sandwich" assay.

Secondary antibodies are polyclonal or monoclonal antibodies to the primary antibody.

Methods for producing primary and secondary antibodies are well known in the art and no further details are necessary. The antibodies may be affinity-purified or unpurified.

The surface on which antibody is coated may be any one of a wide variety of materials. As is known in the art, such materials include polymers, such as polystyrene, polyethylene, polypropylene, polytetrafluoroethylene, polyamides, polyacrylamides, polyvinylchloride, etc.; glass, bacterial cells; ion exchange resins, etc. Such solid carriers are known in the art and no further details in this respect are necessary. The surface substrate may be in the form of a sheet, film, solid particles, tubing, cups or test tubes with test tubes preferred. Most preferred are polypropylene or polystyrene test tubes.

Buffers are used to maintain the physiological activity of the molecules and are known in the art. Buffers may include, for example, carbonate, borate, Tris, glycine, and phosphate buffered saline (PBS).

The concentration of the secondary antibody may be about 0.5–6.0 µg/mL with 1–4 µg/mL preferred and 1–2 µg/mL most preferred. The secondary antibody can be unpurified or some purified fraction of IgG. All classes of immunoglobulin are acceptable but IgG is preferred. The affinity purified antisera to Fc fragment of IgG's are most preferred.

The primary antibody requires no special treatment and may be used in a concentration of about 5 ng–20,000 ng/mL, with about 20–3000 ng/mL preferred and about 20–200 ng/mL most preferred.

The blocking agents may include protein such as bovine serum albumin, gelatin, or casein. The blocking agent is preferably a bovine serum albumin (BSA) solution in a concentration from about 0.1–50 mg/mL, with about 0.25–25 mg/mL preferred, and 1–10 mg/mL most preferred.

The use of a polyol solution along with the BSA solution is preferred. Polyols are believed to increase temperature stability of the antibody. In general, sugars such as dextrose or glycols have been used in this capacity, and no other details of their use are necessary. Sugars such as dextrose may be used in a concentration of about 0.1–100 mg/mL, with about 2–100 mg/mL preferred, and about 10–50 mg/mL most preferred.

The invention utilizes a two-step coating process involving the precoating of a substrate with a secondary antibody and then a coating with primary antibody mixed with a blocking agent and optionally, a polyol. The precoating may be carried out at a temperature of from about 18° C. to about 24° C., preferably from about 20° C. to about 22° C. with a time of from about 6 to about 24 hours. A coating with primary antibody with, for example, BSA and dextrose, may be carried out at a temperature of from about 18° C. to about 24° C., preferably from about 20° C. to about 22° C. for a time of from about 16 to about 24 hours. A relative humidity (RH) of 30 to 60% is acceptable, but 40±5% is preferred. When compared with previous coating methods, the process requires fewer steps and exhibits improved performance in immunoassays. Since the primary (capture) antibody binds only to secondary antibody, it does not compete with blocking agent for free surface area. In addition, if the secondary antibody is Fc specific, the capture antibody is bound in the proper orientation. The primary antibody can bind to the surface of the substrate but does not compete with the blocking agent such as BSA which may be at a 1000 fold excess or more.

Coating procedures, per se, are known in the art, and in general, involve incubating a substrate surface with an antibody-containing solution whereby antibodies become immobilized on the surface. This may be carried out at room temperature, although higher or lower temperatures may be employed. The coating process is also concentration dependent. Higher concentration of antibody can decrease coating time, but this tends to be cost prohibitive for a manufacturing process.

In one embodiment, a polypropylene test tube may be precoated by placing a first solution containing secondary antibody within the tube and incubating for about 24 hours. The first solution is aspirated and a second solution containing primary antibody, in 5% dextrose and 1% BSA is introduced, followed by incubation for about 24 hours. After incubation, the second solution is aspirated and the tube is allowed to dry.

The invention may be illustrated by the following non-limiting examples.

EXAMPLE 1

COMPARISON OF COATING PROCEDURES TSH

I. Preparation of Coated Tubes

In the coating procedures, polypropylene tubes were used and all coating solutions were made using a 100 mM sodium phosphate buffer, pH 7.50. Each coating step generally required 16 to 24 hours. Spent solutions were removed by aspiration. Upon completion of the tube coating processes, tubes were stored in ziplock bags with dessicant. This process has been successfully scaled up.

A. Standard Coating Procedure

Primary antibody was coated directly onto the tubes as follows: Tubes were coated with 1.0 μg/mL of affinity purified goat anti-human TSH-β2 polyclonal antibody.

B. Cocoat/Postcoat

Primary and secondary antibodies were cocoated directly onto the tubes, followed by postcoating with blocking agent to block spaces on the tubes which were not coated with antibody: Tubes were coated with 0.1 μg/mL of affinity purified goat anti-human TSH-β2 polyclonal antibody along with 2 μg/mL RAGGIG (rabbit anti-goat IgG and Fc fragment specific antibody). The postcoating contained 1% BSA and 5% dextrose.

C. Precoat/Coat/Postcoat

Tubes were first precoated with 2 μg/mL of RAGGIG (rabbit anti-goat IgG, Fc fragment specific) secondary antibody. The tubes were then coated with 0.1 μg/mL of affinity purified goat anti-human TSH-β2 polyclonal antibody primary antibody, followed by a postcoating containing 1% BSA and 5% dextrose.

D. Precoat/Coat With Blocking Agent

Tubes were first precoated with 2 μg/mL of RAGGIG (rabbit anti-goat IgG, Fc fragment specific) secondary antibody. The tubes were then coated with 0.1 μg/mL affinity purified goat anti-human TSH-β2 polyclonal antibody primary antibody, along with 1% BSA blocking agent.

II. Nonisotopic Liposome Assay for TSH

Principle of Assay Methods

The nonisotopic assay is based on the use of artificial membranes known as liposomes. The liposomes incorporate fluorescent dye and are formulated with a surface-bound monoclonal antibody to TSH. The test also uses plastic tubes coated with an antibody having a different TSH antigenic site. In the presence of TSH, both antibodies (i.e. those on the liposomes and those on the plastic tube) bind to the TSH, forming an immobilized "sandwich". After incubation, the unbound liposomes are removed, and bound liposomes are lysed with detergent. The fluorescence resulting from the release of encapsulated dye is directly proportional to the concentration of TSH in the serum.

A. Preparation of Liposome Tracer

A monoclonal anti-human TSH is digested and the F(ab') fraction of the antibody is coupled to N-maleimidocaproyl liposomes (MC liposomes). The resulting liposome stock is then diluted to a titer of 1/100 in a filtered 0.1M phosphate buffer, pH 7.5. The buffer also contains 0.8% BSA, 6 mM EDTA, 0.2% sodium azide, 5% casein and 1% glycerol. The liposomes incorporate fluorescent dye.

B. Assay Procedure

Description of Components/Formulations

Standards are formulated from a barbital buffer containing 3.5% BSA, NaCl and preservatives. The h-TSH spiked into the matrix is a lyophilized commercial preparation which has been calibrated to WHO/MRC hTSH. Standards containing 0.0, 0.3, 2.0, 8.0, 20.0, and 50.0 μIU/MLTSH are used in the generation of a standard curve. Controls were from the RIATRAC 7000 series which have been tested extensively.

The wash solution contains 0.15M sodium chloride, 0.1% sodium azide, and 0.2% BSA in a sodium phosphate buffer, pH 7.4.

The lysing solution is a 2.1% aqueous solution of Lubrol Px with 0.1% cialit.

The tubes prepared by the various coating procedures above in (I) were used in assays according to the following procedure:

1. Add 200 μL test sample to coated tube.
2. Add 500 μL tracer to coated tube.
3. Incubate reaction mixture at 45° C. for 2 hours.
4. Agitate reaction mixture at 240 rpm while incubating.
5. Aspirate reaction mixture after completing incubation.
6. Add 2 mL wash to tube with Eppendorf pipette.
7. Aspirate wash solution from tube.
8. Repeat steps 6 and 7 two more times.
9. Add 2 mL lysing solution to washed tube.
10. Vigorously vortex tubes containing solution.
11. Wait 5 minutes and revortex.
12. Measure fluorescence on fluorometer.

| Assay Summary | |
|---|---|
| Sample Size | 200 μL |
| Tracer Volume | 750 μL |
| Incubation Time | 2 hours |
| Mixing Rate | 240 rpm |

The dynamic range is defined as the ratio of the fluorescent signals of a 20.0 μIU/ml standard divided by a 0.0 μIU/ml standard. The results are summarized in Table 1.

TABLE 1

| Comparison of Coating Procedures | | |
|---|---|---|
| Coat Procedure | pAb [μg/mL] | Dynamic Range |
| A Std Coat | 1.0 | 1.2 (2 Expts) |
| B Cocoat/Postcoat | 0.1 | 4.9 (2 Expts) |
| C Precoat/Coat/Postcoat | 0.1 | 14.2 (2 Expts) |
| D Precoat/Coat with BSA | 0.1 | 27.8 (3 Expts) |

Definitions
Std Coat: Primary Ab is coated directly onto the tube.
Cocoat: Primary and secondary Ab are simultaneously coated onto tube.
Postcoat: Sites on tube that are not coated with Ab are blocked with blocking agent.
Precoat: Secondary Ab is precoated onto the tube before coating with primary Ab.
Coat: Primary Ab is applied to the surface of tube.
Rinse: Buffer containing no Ab's.

EXAMPLE 2

EFFECT OF THE SEQUENCE OF BLOCKING AGENT COATING ON DYNAMIC RANGE

Tubes were precoated with 1.0 mL of secondary antibody (RAGGIG at 2 μg/mL) for 24 hours followed by coating with 1.0 mL of primary antibody goat anti-human β-TSH antibody following the procedures described in Example 1(I). Tubes were coated with or without 1% BSA and 5% dextrose in the coat or postcoat as indicated. The tubes were used in assays as described in Example 1(II) and the dynamic ranges determined. The results are summarized in Table 2.

TABLE 2

| Coat Procedure | Dynamic Range |
| --- | --- |
| A. Precoat/Coat/Rinse (No BSA) | 15.1 |
| B. Precoat/Coat/Postcoat | 14.2 |
| C. Precoat/Coat (No BSA) | 13.0 |
| D. Precoat/Coat with BSA | 27.8 |

The results show that the addition of BSA in the primary antibody coating step of the two step procedure of the invention (Precoat/Coat) has a significant impact on dynamic range. Addition of the BSA in a postcoat step, however, offers little benefit in increasing the dynamic range.

EXAMPLE 3

Tubes prepared using the inventive precoat/coat method as described in Example 1(I)(D) were evaluated using an RIA tracer in an IRMA format. The RIA assay reagents were obtained from the Becton Dickinson TSH MAb I$^{25}$ Solid Phase kit. The assays were performed according to the following procedure.

Thyroid Stimulating Hormone MAb [$^{125}$I]

Solid Phase Component System

For the Quantitative Determination of Human Thyroid Stimulating Hormone (TSH) in Serum or Plasma.

Assay Procedure

In the following protocol the standards and patient samples must be run in duplicate. Control sera should be run concurrently with patient samples. The standard curve and the clinical determinations must be run simultaneously.

All reagents and samples must be brought to room temperature before use, but should not be left at this temperature longer than is necessary. Sterile distilled water is recommended for the wash steps.

1. If data reduction techniques require total counts, label two polystyrene tubes accordingly and set aside.
2. Number Antibody-Coated Tubes from 1-14 for the standard curve and two for each clinical sample and control to be assayed.
3. Add 200 μL TSH Standards and clinical samples to tubes.
4. Add 500 μL TSH Tracer Solution to all tubes. Vortex briefly. Cover tubes.
5. Incubate at 37 ±1° C. in a water bath for 3.0 hours.
6. Remove all tubes from the water bath and uncover them.
7. Aspirate or decant. Add 2.0 mL distilled water.
8. Repeat step 7. Aspirate or decant a final time.
9. Count the radioactivity in these tubes and total count tubes (if needed) in a gamma counter for one minute.

| Tube No. | Standard (μL) | Patient Serum (μL) | Tracer (μL) | Incubate | Wash |
| --- | --- | --- | --- | --- | --- |
| 1, 2 | 200A | — | 500 | — | |
| 3, 4 | 200B | — | 500 | Vortex | Aspirate |
| 5, 6 | 200C | — | 500 | and | and wash |
| 7, 8 | 200D | — | 500 | incubate | all tubes |
| 9, 10 | 200E | — | 500 | all tubes | 2 times |
| 11, 12 | 200F | — | 500 | at 37° C. | except |
| 13, 14 | 200G | — | 500 | for 3.0 | total |
| Controls and Patient Samples | | 200 | 500 | hours | count if used |

Calculation of Results

Automated Calculation

Automated data reduction techniques may be used to calculate TSH results. Point-to-point interpolation, four parameter logistic fit or other types of curve fitting programs may be utilized.

Manual Calculations

1. Calculate the average cpm for tubes 1-2. Standard A.
2. Subtract the average cpm for tubes 1-2 from each other succeeding tube cpm to obtain a correct cpm.
3. The standard curve may be plotted using the corrected cpm for each standard level on the y-axis versus the standard concentration on the x-axis using log-log graph paper.

The results are shown in Table 3.

TABLE 3

| | Counts Per Minute | |
| --- | --- | --- |
| | RIA Tubes | New Tubes |
| TSH Concn [μIU/ml] | | |
| 0.00 | 602.7 | 259.7 |
| 0.22 | 790.5 | 490.0 |
| 1.04 | 1558.0 | 1134.0 |
| 3.71 | 4330.0 | 3503.0 |
| 8.38 | 9005.0 | 7662.0 |
| 35.50 | 23350.0 | 24445.0 |
| 97.00 | 40536.0 | 42014.0 |
| Accuracy | | |
| RIATRAC 1 | 3.81 μIU | 3.10 μIU |
| RIATRAC 2 | 7.81 μIU | 7.81 μIU |
| RIATRAC 3 | 26.24 μIU | 28.97 μIU |
| RIA Assay Reagents | | |
| RIA Tubes: BD AN 1948A | | |
| RIA Tracer: RIA AN2228 | | |
| RIA Stds: AN1505 | | |

The results show that an RIA tracer can be used in an assay which utilizes tubes coated by the process of the invention.

EXAMPLE 4

COMPETITIVE ASSAY USING NON-PURIFIED PRIMARY ANTIBODY

Tubes were coated as described in Example 1(I)(D) except that monoclonal primary antibody in ascites was used instead of polyclonal primary antibody, and the primary antibody was not purified before coating.

The tubes used in this assay were prepared according to the standard coating procedure and the new two step process. The coating buffer in the standard coat process was 100 mM phosphate, pH 7.5 into which was diluted ascites fluid containing the monoclonal antibody. The titer was 1/10,000. Tubes were coated with 1.0 mL antibody solution for 24 hours before being processed. With the new coating process, the tubes were first precoated with 1.0 mL of 2μg/mL GAMIgG, Fc specific before coating with 1.0 mL ascites fluid containing 1/500,000 MAb.

The tubes were used in a nonisotopic liposome assay for T uptake using a competitive format. In this thyroid uptake (T uptake) test procedure, a fixed quantity of thyroxine and thyroxine conjugate liposomes are present in the assay buffer. Assay tubes were coated with an anti-$T_4$ monoclonal antibody (MAb) using the standard coat and the new precoat-coat procedure. The MAb is capable of binding both the liposome conjugate and the thyroxine. The binding proteins, including TBG, present in the serum of the reference standard and the unknown will bind the thyroxine, but not the thyroxine-liposomes. The amount of thyroxine left unbound in the serum will compete with the liposomes for the antibody on the tube. If the binding capacity of the unknown serum TBG is less than the reference standard's, the uptake of thyroxine will be higher, displacing liposomes.

After incubation, the tubes were washed to remove any nonspecifically bound liposomes and a detergent solution was used to disrupt the liposome membrane, releasing fluorescent dye. The fluorescence was measured in a fluorometer and the uptake value determined by the following equation:

$$\text{Uptake(Unknown)} = \frac{\text{Signal(Ref)} - \text{Signal(Blank)}}{\text{Signal(UNK)} - \text{Signal(Blank)}} \cdot \text{Uptake (Ref)}$$

| Nonisotopic Liposome Assay For T Uptake Using A Competitive Assay Format | |
|---|---|
| Assay Buffer | 0.1M Phosphate pH 7.4 |
| | 0.14 m NaCl |
| | 0.04% Salicylate |
| | 0.05% BSA |
| | 0.25% μg $T_4$ Spike |
| Liposome | Becton Dickinson Advanced Diagnostics |
| | Lot #1065-32-2 at 1/100 Titer |

Assay Procedure
1. Add 25 μl Sample to coated polypropylene tube.
2. Add 1000 μl tracer to coated tube.
3. Vortex all tubes for 2 to 3 seconds.
4. Incubate reaction mixture at 45 deg. for 30 minutes.
5. Aspirate reaction mixture after completing incubation.
6. Add 5 mL wash to tube with Brinkman repipettor.
7. Aspirate wash solution from tube.
8. Repeat step 6 and 7 two more times.
9. Add 2 mL lysing solution to washed tube.
10. Vigorously vortex tubes containing solution.
11. Wait 5 minutes and revortex tubes.
12. Measure fluorescence on fluorometer.

| Assay Summary | |
|---|---|
| Sample size | 25 μL |
| Tracer Volume | 1000 μL |
| Incubation Time | 30 minutes |
| Mixing Rate | stationary |

The results are shown in Table 4.

TABLE 4

| Precoat/Coat Tubes and Std Coat Tubes Evaluated in a T Uptake Competitive Assay | | |
|---|---|---|
| Coating Process Primary Ab Titer μg/mL of $T_4$ | Std Coat 1/10,000 | Precoat/Coat 1/500,000 |
| | Fluorescence Units | |
| 0.0 | 6258.0 | 6416.5 |
| 0.5 | 4423.5 | 5666.0 |

TABLE 4-continued

| Precoat/Coat Tubes and Std Coat Tubes Evaluated in a T Uptake Competitive Assay | | |
|---|---|---|
| Coating Process Primary Ab Titer μg/mL of $T_4$ | Std Coat 1/10,000 | Precoat/Coat 1/500,000 |
| | Fluorescence Units | |
| 2.0 | 4258.5 | 4288.0 |
| 4.0 | 3540.5 | 3663.0 |
| 8.0 | 3122.0 | 3194.0 |
| 32.0 | 2438.5 | 2736.5 |

The results show that the amount of antibody required for an equivalent response was reduced by 50 fold when the new coating process was used.

EXAMPLES 5-8

Conditions in the precoat and coat step were varied to determine their impact on the assay response. Conditions are tabulated in each example, and conclusions are summarized below each example. The coated tubes were prepared according to the procedure of Example 1(I)(D) and assayed according to procedures described in the Principle of Assay Methods given in Example 1. Assay components are described in the section on Description of Components/Formulations also given in Example 1.

| Precoating With Different Secondary Ab's | | |
|---|---|---|
| | Antibodies on Tube | Source |
| GAH TSH | Primary Ab | Ventrex |
| RAGGIG | Secondary Ab | Jackson Immunoresearch |
| GAH TSH | Primary Ab | OEM (A.P.) |
| RAGGIG | Secondary Ab | Jackson Immunoresearch |
| RAH TSH | Primary Ab | Ventrex |
| GARGIG | Secondary Ab | Jackson Immunoresearch |
| RAH TSH | Primary Ab | OEM (A.P.) |
| GARGIG | Secondary Ab | Jackson Immunoresearch |

TABLE 5

| Secondary Ab | Primary Ab | Ab[μg/mL] | Dynamic Range |
|---|---|---|---|
| RAGGIG | Ventrex Goat | [1.00] | 9.7 |
| " | " | [0.50] | 8.7 |
| " | " | [0.25] | 9.1 |
| GARGIG | Ventrex Rabbit | [1.00] | 8.5 |
| " | " | [0.50] | 8.9 |
| " | " | [0.25] | 13.2 |
| RAGGIG | OEM Goat | [0.20] | 17.0 |
| " | " | [0.10] | 16.0 |
| " | " | [0.05] | 13.2 |
| GARGIG | OEM Rabbit | [0.20] | 13.2 |
| " | " | [0.10] | 11.0 |
| " | " | [0.05] | 8.6 |

A precoat consisting of RAGGIG or GARGIG were each coated against two different primary Ab's. The coat buffer consisted of 100 mM sodium phosphate, pH 7.45 with 1% BSA and 5% dextrose. The Ab on the liposome was a MAH TSH supplied by Becton Dickinson Research Center, Clone 291.

Observation

All four antibody combinations gave displacement.

EXAMPLE 6

| Response at Low Concentrations of Primary Antibody Using New Precoat Method |
|---|
| Antibodies on Tube |

-continued

Response at Low Concentrations of Primary Antibody Using New Precoat Method

| Description | Type |
|---|---|
| GAH TSH | Primary Ab |
| RAGGIG; 2 μg/mL | Secndary Ab |
| Antibody on Liposome | |
| MAH TSH | |

TABLE 6

| PAb[μg/mL] | Dynamic Range |
|---|---|
| 0.050 | 12.5 |
| 0.025 | 12.0 |
| 0.020 | 11.5 |
| 0.010 | 10.7 |
| 0.005 | 6.9 |

Observation

Precoated tubes at 10 ng/tube of primary antibody gave measureable displacement. In contrast, tubes coated with Std coat method barely gave displacement at 100× greater concentration.

EXAMPLE 7

I. Varying Concn Primary Ab, pH, and Ionic Strength of Coat Buffer

| Antibodies on Tube | |
|---|---|
| Description | Type |
| GAH TSH | Primary Ab |
| RAGGIG | Secondary Ab |
| Antibody on Liposome | |
| MAH TSH | |
| Precoat Buffer | |
| 2 μg/ml RAGGIG in 100 mM Phos., pH 7.45. | |

TABLE 7

| Coat Buffer | PAb[μg/mL] | pH, 8.0 Dynamic Range | pH, 7.45 Dynamic Range |
|---|---|---|---|
| 500 mM Phos | 0.20 | 15.0 | 14.7 |
| 250 mM | " | 17.9 | 14.8 |
| 100 mM | " | 17.4 | 17.8 |
| 500 mM Phos | 0.10 | 13.3 | 9.5 |
| 250 mM | " | 17.8 | 9.2 |
| 100 mM | " | 20.3 | 10.7 |
| 500 mM Phos | 0.05 | 17.2 | 13.6 |
| 250 mM | " | 10.1 | 10.4 |
| 100 mM | " | 12.1 | 12.4 |

Observation

Changes in the Ab concentration were not sensitive to changes in ionic strength or pH of the coat buffer. A coat buffer pH of 8.0 gives better dynamic range than pH 7.45 under these conditions.

II. Varying pH, Ionic Strength, and Counter-ion of Coat Step

| Antibodies on Tube | |
|---|---|
| Description [μg/mL] | Type |
| GAH TSH, [0.20] | Primary Ab |
| RAGGIG; [2.0] | Secondary Ab |
| Antibody on Liposome | |
| MAH TSH | |

TABLE 8

| Coat Buffer | mM Concn | pH | Dynamic Range |
|---|---|---|---|
| Phosphate | 10 | 7.45 | 14.3 |
| " | 100 | " | 15.1 |
| " | 300 | " | 17.9 |
| " | 500 | " | 15.2 |
| Phosphate | 300 | 6.75 | 12.4 |
| " | " | 8.50 | 10.1 |
| Glycine | 300 | 9.60 | 6.1 |

Observation

The dynamic range of the tubes appear to be relatively insensitive to pH changes in the coat buffer from 6.75 to 8.50 and ionic strength changes between 10 and 500 mM.

Although the 300 mM glycine pH 9.6 is not a preferred coat buffer with this antibody, it is satisfactory with other antibodies under other conditions as shown below.

EXAMPLE 8

Varying Concn Secondary Ab in a Glycine Precoat and Varying Ionic Strength of Cocoat

| Antibodies on Tube | |
|---|---|
| Description | Type |
| GAH TSH | Primary Ab |
| RAGGIG | Secondary Ab |
| Antibody on Liposome | |
| MAH TSH | |

TABLE 9

| Precoat Buffer | mM | pH | Ab [μg/mL] | Coat Buffer | mM | pH | PAb [μg/mL] | Dynamic Range |
|---|---|---|---|---|---|---|---|---|
| Glycine | 300 | 9.6 | [1.0] | Phos | 100 | 7.45 | 0.2 μg/mL | 15.3 |
| " | " | " | [2.0] | " | " | | | 15.0 |
| " | " | " | [1.0] | Phos | 10 | 7.45 | 0.2 μg/mL | 15.5 |
| " | " | " | [2.0] | " | " | | | 15.1 |

Observation

In addition to the standard precoat using phosphate buffer, the tube response is satisfactory using 1 or 2μg/mL of secondary antibody in 300 mM glycine, pH 9.6 precoat and varying ionic strength of phosphate coat buffer.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A process for coating an antibody on a substrate, consisting of:

(i) contacting a secondary antibody with a substrate surface which is capable of binding said secondary antibody to form a secondary antibody-coated substrate;

(ii) contacting said secondary antibody-coated substrate with a primary antibody to which the secondary antibody is specific, along with a blocking agent.

2. The process of claim 1 wherein the substrate is a plastic test tube.

3. The process of claim 1 wherein said secondary antibody has a concentration of from about 0.5 to about 6 μg/mL.

4. The process of claim 1 wherein said primary antibody has a concentration of from about 10 to about 500 nanograms/mL.

5. The process of claim 1 wherein said blocking agent is selected from the group consisting of bovine serum albumin, gelatin and casein.

6. The process of claim 5 wherein said blocking agent is bovine serum albumin in a concentration of from about 1.0 mg/mL to about 50 mg/mL.

7. The process of claim 1 further comprising a stabilizer in the second contacting step (ii).

8. The process of claim 1 wherein the secondary antibody is unpurified.

9. The process of claim 1 wherein the primary antibody is unpurified.

10. The process of claim 9 wherein the primary antibody is in ascites fluid.

11. An article suitable for use in an immunoassay comprising a substrate coated with secondary antibody bound to primary antibody according to the process of claim 1.

12. The process of claim 1 wherein the substrate coated with secondary antibody bound to primary antibody is suitable for use in a competitive assay.

13. The process of claim 12 wherein the competitive assay is for an antigen selected from the group consisting of $T_3$, $T_4$, digoxin and theophylline.

14. The process of claim 1 wherein the substrate coated with secondary antibody bound to primary antibody is suitable for use in a sandwich assay.

15. The process of claim 14 wherein the sandwich assay is for thyroid stimulating hormone.

* * * * *